United States Patent
Wheatley et al.

(10) Patent No.: US 12,090,203 B2
(45) Date of Patent: Sep. 17, 2024

(54) SURFACTANT MICROBUBBLES COMPOSITIONS AND PROCESS FOR PREPARING THEREOF

(71) Applicants: Drexel University, Philadelphia, PA (US); Thomas Jefferson University, Philadelphia, PA (US)

(72) Inventors: Margaret A. Wheatley, Media, PA (US); John Robert Eisenbrey, Wayne, PA (US); Brian E. Oeffinger, Philadelphia, PA (US); Purva Vaidya, Flushing, NY (US)

(73) Assignees: Drexel University, Philadelphia, PA (US); Thomas Jefferson University, Philadelphia, PA (US)

(*) Notice: Subject to any disclaimer, the term of this patent is extended or adjusted under 35 U.S.C. 154(b) by 321 days.

(21) Appl. No.: 17/595,709

(22) PCT Filed: May 29, 2020

(86) PCT No.: PCT/US2020/035254
§ 371 (c)(1),
(2) Date: Nov. 23, 2021

(87) PCT Pub. No.: WO2020/243523
PCT Pub. Date: Dec. 3, 2020

(65) Prior Publication Data
US 2022/0249667 A1    Aug. 11, 2022

Related U.S. Application Data

(60) Provisional application No. 62/853,926, filed on May 29, 2019.

(51) Int. Cl.
*A61K 41/00* (2020.01)
*A61K 9/107* (2006.01)
(Continued)

(52) U.S. Cl.
CPC ........ *A61K 41/0033* (2013.01); *A61K 9/1075* (2013.01); *A61K 31/416* (2013.01);
(Continued)

(58) Field of Classification Search
None
See application file for complete search history.

(56) References Cited

U.S. PATENT DOCUMENTS

| | | |
|---|---|---|
| 4,844,882 A | 7/1989 | Widder et al. |
| 5,352,436 A | 10/1994 | Wheatley et al. |

(Continued)

OTHER PUBLICATIONS

Zhang et al. (Docetaxel-loaded lipid microbubbles combined with ultrasound-triggered microbubble destruction for targeted tumor therapy in MHCC-H cells, 2016, OncoTargets and Therapy, 7:4763-4771) (Year: 2016).*

(Continued)

*Primary Examiner* — Soren Harward
*Assistant Examiner* — Kaila A Craig
(74) *Attorney, Agent, or Firm* — Saul Ewing LLP; Kathryn Doyle; Domingos J. Silva

(57) ABSTRACT

The present invention provides methods for preparing acoustically-sensitive microbubbles. The method includes the steps of: i) preparing a first surfactant solution comprising a first micelle-forming surfactant at a concentration above the critical micelle concentration (CMC); ii) adding one or more pharmaceutical compounds in a solvent to the first surfactant solution, thereby loading the micelles with the one or more pharmaceutical compounds; iii) preparing a second surfactant solution comprising a second surfactant, wherein the second surfactant comprises one or more matrix forming surfactants; iv) adding heat to the second surfactant solution to melt the surfactant and allowing the mixture to cool under rapid stirring; v) combining the second surfactant solution with the loaded micelles; vi) purging the surfactant (Continued)

mixture with a purging gas; vii) agitating the purged mixture under a constant stream of the purging gas; and, viii) separating the formed microbubbles by size.

17 Claims, 9 Drawing Sheets

(51) Int. Cl.
*A61K 31/416* (2006.01)
*A61K 47/14* (2017.01)
*A61K 47/18* (2017.01)
*A61K 47/22* (2006.01)
*A61K 49/00* (2006.01)

(52) U.S. Cl.
CPC ............ *A61K 47/14* (2013.01); *A61K 47/186* (2013.01); *A61K 47/22* (2013.01); *A61K 49/0082* (2013.01)

(56) References Cited

U.S. PATENT DOCUMENTS

| | | |
|---|---|---|
| 6,416,740 B1 | 7/2002 | Unger |
| 7,875,677 B2 | 1/2011 | Jackson et al. |
| 2012/0109045 A1 | 5/2012 | Wrenn et al. |
| 2012/0237450 A1* | 9/2012 | Wheatley ............ A61K 49/223 424/9.5 |
| 2016/0059036 A1* | 3/2016 | Eisenbrey ............ A61K 9/0009 600/1 |

OTHER PUBLICATIONS

Sadoqi et al. (Investigation of the micellar properties of the tocopheryl polyethylene glycol succinate surfactants TPGS 400 and TPGS 1000 by steady state fluorometry, Feb. 20, 2009, Journal of Colloid and Interface Science, 333:585-589) (Year: 2009).*

Milane et al. (Pharmacokinetics and biodistribution of lonidamine/paclitaxel loaded, EGFR-targeted nanoparticles in an orthotopic animal model of multi-drug resistant breast cancer, 2011, Nanomedicine: Nanotechnology, Biology, and Medicine, 7:435-444) (Year: 2011).*

International Search Report and Written Opinion, International Patent Application No. PCT/US2020/035254, Sep. 4, 2020.

Milane, L., et al., "Biodistribution and Pharmacokinetic Analysis of Combination Lonidamine and Paclitaxel Delivery in an Orthotopic Animal Model of Multi-drug Resistant Breast Cancer Using EGFR-Targeted Polymeric Nanoparticles", Nanomedicine 7(4), Aug. 2011.

* cited by examiner

US 12,090,203 B2

SURFACTANT MICROBUBBLES COMPOSITIONS AND PROCESS FOR PREPARING THEREOF

CROSS-REFERENCE TO RELATED APPLICATION(S)

This application is a national phase application under 35 U.S.C. 371 of International Application No. PCT/US2020/035254, filed May 29, 2020, which claims the benefit of priority under 35 U.S.C. § 119(e) to U.S. Provisional Patent Application Ser. No. 62/853,926, filed May 29, 2019, the contents of which are incorporated by reference herein in their entirety.

STATEMENT REGARDING FEDERALLY SPONSORED RESEARCH OR DEVELOPMENT

This invention was made with government support under CA190926 and EB026881 awarded by the National Institutes of Health. The government has certain rights in the invention.

BACKGROUND OF THE INVENTION

Many cancers result in solid tumors having hypoxic regions. Among them is breast cancer, which is the second most prevalent form of cancer globally. Treatment of solid tumors including breast tumors often involves radiation therapy. The efficacy of this treatment is limited by the presence of hypoxic (oxygen deficient) regions within the tumor, leading to poor clinical outcomes.

SUMMARY OF THE INVENTION

One aspect of the invention provides a method for preparing acoustically-sensitive microbubbles. The method includes: (i) preparing a first surfactant solution comprising a first micelle-forming surfactant at a concentration above the critical micelle concentration (CMC); (ii) adding one or more pharmaceutical compounds in a solvent to the first surfactant solution, thereby loading the micelles with the one or more pharmaceutical compounds; (iii) preparing a second surfactant solution comprising a second surfactant, wherein the second surfactant comprises one or more matrix-forming surfactants; (iv) adding heat to the second surfactant solution to melt the one or more matrix-forming surfactants and allowing the mixture to cool under rapid stirring; (v) combining the second surfactant solution with the loaded micelles; (vi) purging the surfactant mixture with a purging gas; (vii) agitating the purged mixture under a constant stream of the purging gas; and (viii) separating the formed microbubbles by size.

This aspect of the invention can have a variety of embodiments. The method can further include (ix) freeze-drying and capping the separated microbubbles under a vacuum. The method can further include (x) reinflating the freeze-dried microbubbles with a filling gas. The filling gas can include oxygen.

The first surfactant can include: TPGS, hexadelyltrimethylammonium bromide (CTAB), didodecyldimethylammonium bromide (DDAB) and mixtures thereof.

The second surfactant can include sorbitan monostearate, sorbitan fatty acid esters, sorbitan monopalmitate, (+) A tolopherol acid succinate (vitamin E) and mixtures thereof. The second surfactant can be solid at room temperature. The second surfactant can be immiscible in water.

The drug-loaded microbubble solution can have a drug-loading efficiency of about 10%.

The CMC can be 0.02 wt % at 37° C.

The one or more pharmaceutical compounds can include one or more chemotherapeutic agents. The one or more chemotherapeutic agents can include lonidamine.

The pharmaceutical compound can include one or more tracing agents. The one or tracking agents can include one or more lipophilic dyes. The one or more lipophilic dyes can be selected from: Nile Red and DiI.

The microbubbles are acoustically-sensitive.

In step (viii), the size of the separated microbubbles can be below 10 μm in diameter.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 2A depicts a dose response curve. FIG. 2B depicts a time response curve.

FIG. 5, Panel B depicts a light micrograph of $SE61_{O2}$ by the standard method and FIG. 5, Panel C depicts a light micrograph of $SE61_{O2}$ by the micelle method. Scale bar=20 μm FIG. 6, Panel A depicts $^1H$ NMR spectrum for SPAN® 60 (Seppic). FIG. 6, Panel B depicts $^1H$ NMR spectrum for TPGS. The dashed line indicates groups and peaks of interest, and FIG. 6, Panel C depicts typical integrated $^1H$ NMR spectrum use to determine surfactant ratio in SE61MBs.

DETAILED DESCRIPTION

Ultrasound contrast agents comprised of a sorbitan monostearate (MONTANE® 60) and water-soluble vitamin E (TPGS) shell with an oxygen gas core have been developed for delivery of oxygen to hypoxic tumor sites. However, the current fabrication method for $SE61_{O_2}$ loaded with a hydrophobic drug requires the use of methanol and results in low drug loading that has high inter-batch variability.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed methods.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

Figure 8:
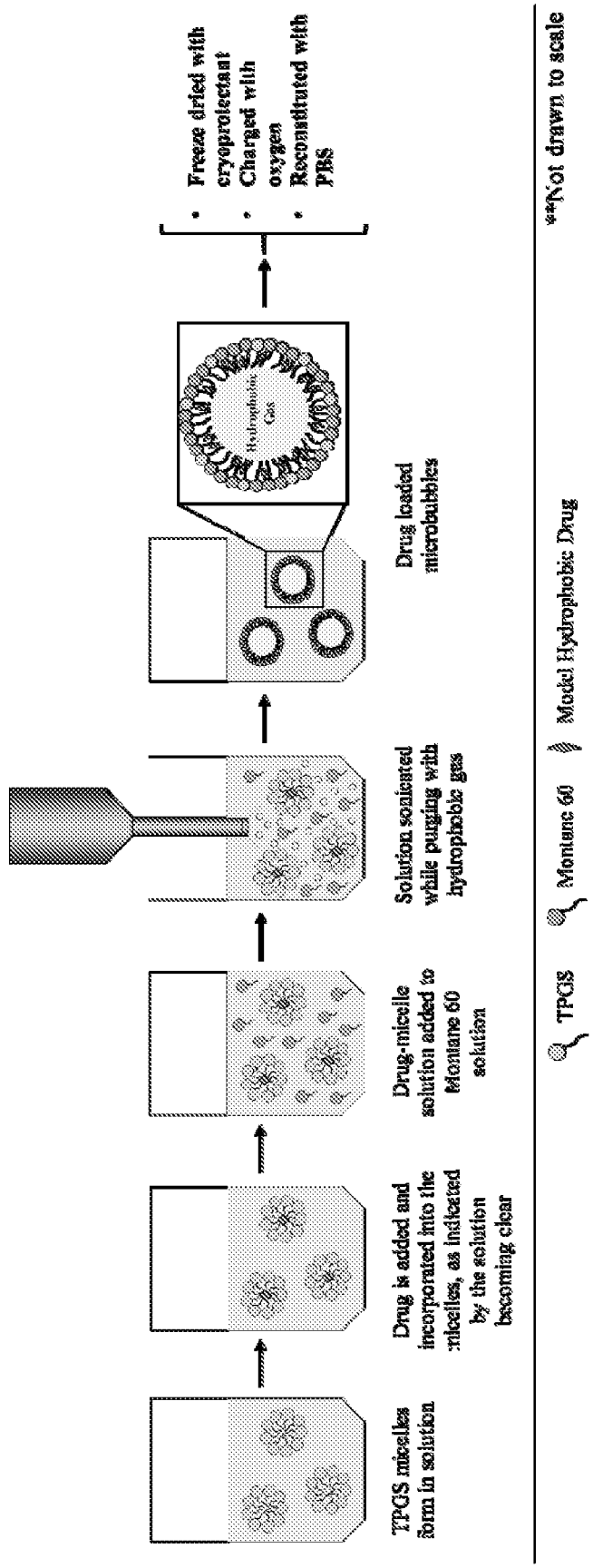
FIG. 8 depicts a schematic illustrating an exemplary method of the present invention.

The present invention provides methods for fabricating acoustically-sensitive biocompatible microbubbles. The microbubbles may deliver therapeutic agents including for example anti-hypoxic agents, chemotherapeutic agents, and the like. The microbubbles may be activated using acoustic waves such as those generated using ultrasound. An exemplary illustration of method of the present invention is shown in FIG. 8. An exemplary method of the present invention is shown in FIG. 9.

Figure 9:
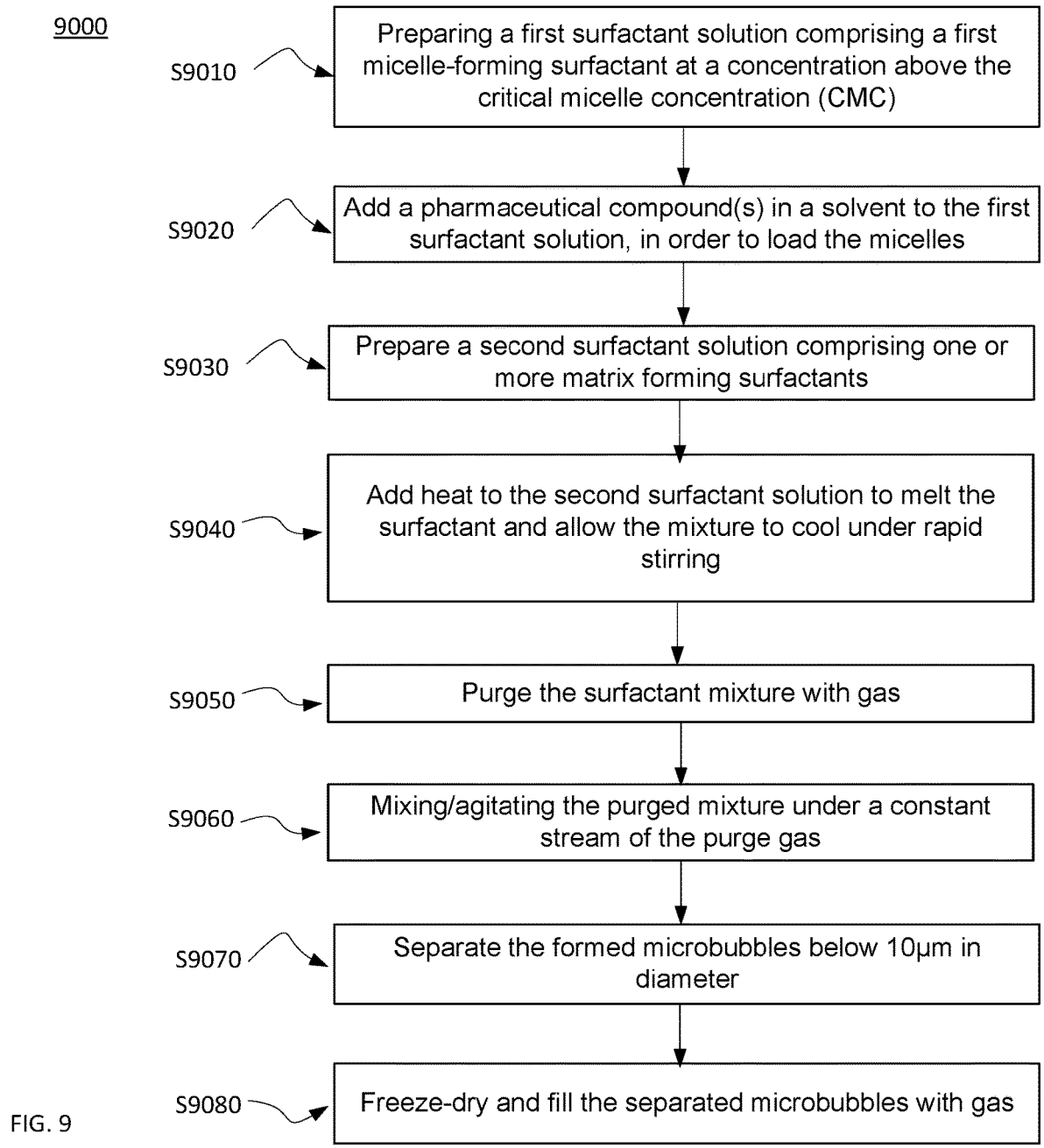
FIG. 9 depicts a flow-chart of an exemplary method according to the present invention.

Referring now to FIG. 9, method 9000 of the present invention provides a method for preparing acoustically-sensitive microbubbles.

Embodiments of step S9010 of method 9000 may include preparing a first surfactant solution comprising a first micelle-forming surfactant at a concentration above the critical micelle concentration (CMC).

The micelle-forming surfactant may include one or more micelle-forming surfactants such as diblock copolymers. The hydrophobic portions of such diblock copolymers may include one or more hydrophobic polymers, such as polyesters, polyanhydrides, polyglycolic acids, polybutrylactones, polyhydroxybutyrates, polylactic acids and polylacaprolactones. The hydrophobic portion of the copolymer may include one or more different hydrophobic polymers in random or block orientation. The hydrophobic portion of a copolymer may have a molecular weight from about 200 to about 5000. The micelle-forming polymers as described herein are capable of forming micelles at very low critical micelle concentrations (CMC), which allows for loading of high concentrations of hydrophobic drugs.

Preferred hydrophilic portions of micelle forming copolymers that may be used in this invention have a molecular weight of about 750 or greater up to about 8000. Preferably, the molecular weight will be in the range of about 1000 or 2000-3000 or 5000. Most preferred is a molecular weight of polymer as the hydrophilic portion of the micelle forming polymer being about 2000.

The first surfactant may include one or more of TPGS, hexadelyltrimethylammonium Bromide (CTAB), didodecyldimethylammonium bromide (DDAB), and mixtures thereof. The first surfactant may include one or more of: medium chain transesterification products of oils and alcohols; monoglycerides or diglycerides or mixtures thereof; polyethylene glycol fatty acid monoesters or diesters or mixtures thereof; polyethylene glycol sorbitan fatty acid esters; polyethylene glycol alkyl ethers; propylene glycol fatty acid monoesters or diesters or mixtures thereof, POE-POP block copolymer fatty acid monoesters or diesters or mixtures thereof, sugar esters; bile salts; fatty acid salts; bisalkyl sulfosuccinate salts; phospholipids; hydrophilic derivatives of phospholipids; fatty acid derivatives of polyamines or polyimines or aminoalcohols or aminosugars or peptides or polypeptides; or mixtures of combinations of one or more of the above surfactants.

Further, more specific examples may include PEG-8 caprylic/capric glycerides (Labrasol, Acconon MC-8), PEG-6 caprylic/capric glycerides (Softgen 767, Acconon CC-6), PEG-12 caprylic/capric glycerides (Acconon CC-12), PEG-35 castor oil (Cremophor EL), PEG-40 castor oil (Cremophor RH), PEG-60 corn glycerides (Crovol M70, lauroyl macrogol-32 glycerides (Gelucire 44/14), PEG-23 lauryl ether (Brij 35), PEG-8 laurate (MAPEG 400 ML), vitamin E TPGS, PEG-20 sorbitan monooleate (Tween 80), PEG-dipalmitoyl phosphatidylethanolamine, PEG-distearoyl phosphatidylethanolamine, bile acid and bile salts, CTAB, DODAB, and sodium bis(2-ethylhexyl) sulfosuccinate.

The CMC of the micelles may include, for example 0.02 wt % at 37° C. The CMC of the micelles may include 0.003% at 22° C. The micelles may have a CMC of up to about 0.001 wt %, from about 0.001 wt % to about 0.005 wt %, from about 0.005 wt % to about 0.01 wt % and any and all increments therebetween at 22° C. The micelles may have a CMC of up to about 0.005 wt %, from about 0.005 wt % to about 0.01 wt %, about 0.01 wt % to about 0.05 wt %, and any and all increments therebetween at 37° C. The first micelle-forming surfactant may be dissolved in one or more warm solutions. The warm solution may include one or more of buffered saline such as phosphate buffered saline (PBS), isotonic saline solution, and the like. The warm solution may have a temperature of about 37° C. The first micelle-forming surfactant may be stirred in the warm solution for up to 20 minutes, at least 20 minutes, from about 20 minutes to about 30 minutes, from about 30 minutes to about 1 hour, up to about 1 hour, from about 1 hour to about 2 hours, from about 2 hours to about 4 hours, from about 4 hours to about 8 hours, from about 8 hours to about 12 hours, from about 12 hours to about 24 hours, from about 24 hours to about 36 hours, from about 36 hours to about 48 hours, or greater than about 48 hours. The first micelle-forming surfactant may be incubated in the warm solution under mixing. The mixing may be performed using, for example, a stir bar and stir plate, a submersion mixer, a vortex, a platform mixer, a platform rocker, a stir rod, and the like. Alternatively, the first micelle-forming surfactant may be incubated in the warm solution under static conditions, or one or more intervals of static and mixing conditions.

Embodiments of step S9020 may include adding one or more pharmaceutical compounds to the micelles formed from the first surfactant solution, thereby loading the micelles with the one or more pharmaceutical compounds. The one or more pharmaceutical compounds may be added as a solution in a solvent. The one or more pharmaceutical compounds may be added to the micelle solution in a solid form such as a powder, a capsule, a tablet, or the like. The one or more pharmaceutical compounds may incorporate into the micelles, as shown in FIG. 8.

The one or more pharmaceutical compounds may include one or more chemotherapeutic agents. The one or more chemotherapeutic agents may include one or more of lonidamine, curcumin, paclitaxel and the like.

The pharmaceutical compound may include one or more tracking agents. The one or tracking agents may include one or more lipophilic dyes. The one or more lipophilic dyes may include one or more of Nile Red, one or more dialkylcarbocyanines such as indocarbocyanine (DiI), cresyl violet, DODCI, rhodamine B, rhodamine DPPE, and the like. The one or more tracking agents may include one or more of nanoparticles such as gold (AuNP), carbon dots, quantum dots, magnetic nanoparticles such as super paramagnetic iron oxide, and the like.

The drug-loaded microbubble solution may include a drug-loading efficiency of about 10%. The drug-loading efficiency may include from about 10% to about 20%, from about 20% to about 30%, from about 30% to about 40%, from about 40% to about 50%, from about 50% to about 60%, from about 60% to about 70%, from about 70% to about 80%, from about 80% to about 90%, or greater than about 90%.

Embodiments of step S9030 may include preparing a second surfactant solution comprising a second surfactant. The second surfactant may include one or more matrix-forming surfactants.

The second surfactant may include one or more of sorbitan monostearate, sorbitan fatty acid esters, sorbitan monopalmitate, (+) A tolopherol acid succinate (vitamin E) and mixtures thereof.

The second surfactant may include one or more amphiphilic compounds: such as fatty acid esters, ethers or amides of alcohols, aminoalcohols, glycols, polyols, saccharides or oligosaccharides or polysaccharides, oxyalkylene oligomers or polymers or block polymers, amines, polyimines, hydroxyalkylamines, hydroxypolyimines, peptides, polypeptides, or hydrophilic derivatives thereof; and hydrophilic derivatives of fatty acids, polyglycerized fatty acids.

The second surfactant may include one or more ionic or zwitterionic surfactants: such as fatty acid salts, bile salts, sulfates, sulfonates, carboxylates, lactylates, phospholipids and derivatives thereof, and quaternary ammonium salts.

The second surfactant may include one or more complexing agents: such as charge-complex agents (for example, fatty acids, organic acids and chelating agents); and inclusion complexing agents (for example, cyclodextrins and derivatives). Some examples include but not limited to: fatty acid monoesters or diesters or mixtures thereof of glycols such as ethylene glycols or propylene glycols or butylenes glycols; monoglycerides or diglycerides or mixtures thereof; polyglycerized fatty acids, polyethylene glycol fatty acid monoesters or diesters or mixtures thereof; POE-POP block copolymer fatty acid monoesters or diesters or mixtures thereof; polyethylene glycol sorbitan fatty acid esters; sorbitan fatty acid esters; ethylene glycol or diethylene glycol or triethylene glycol or polyethylene glycol alkyl ethers; phospholipids and derivatives thereof; PEG-phospholipids; PEGs; alcohols; fatty alcohols; fatty acids; and mixtures of the foregoing solubilizers. The one or more solubilizers may include one or more of: propylene glycol dicaprylate/dicaprate (Captex 200), propylene glycol monocaprylate (Capmul PG-8), propylene glycol caprylate/caprate (Labrafac PG), propylene glycol dicaprylate (Captex 100), propylene glycol diethylhexanoate, propylene glycol monolaurate (Capmul PG-12), glyceryl caprylate/caprate (Capmul MCM), glyceryl monocaprylate (Capmul MCMC-8, Imwitor 308), glyceryl monooleate (Capmul GMO), capric acid monoglyceride (Imwitor 312), PEG-6 corn oil (Labrafil M 2125), sorbitan monooleate (SPAN® 80); sodium lauryl sulfate, sodium taurocholate, lecithin, lyso-lecithin, phosphatidyl glycerol, polyethylene glycol-phosphatidyl ethanolamines, cetyl trimethyl ammonium bromide, lauryl betaine; cyclodextrin (various forms and derivatives thereof); and acetyl triethylcitrate, triethylcitrate, ethyl oleate, ethyl caprylate, triacetin; tetrahydrofurfuryl alcohol PEG ether (glycofurol), m-PEG, diethylene glycol monoethyl ether (Transcutol), diethylene glycol monobutyl ether, ethylene glycol monoethyl ether; ethanol, isopropanol, benzyl alcohol, ethylene glycol, propylene glycol, glycerol, sorbitol, mannitol, polyvinylalcohol, cellulose derivatives; polyethylene glycol (PEG 400 etc.), polypropylene glycol, POE-POP block polymers; pyrrolidones, N-alkylpyrrolidones, N-hydroxyalkylperrolidones, N-methylpyrrolidone, piperidones, N-alkylpiperidones, polyvinylpyrrolidones.

The second surfactant may include any suitable surfactant that is solid at room temperature. The second surfactant may include any suitable surfactant that is immiscible in water.

Embodiments of step S9040 may include adding heat to the second surfactant solution and allowing the mixture to cool under rapid stirring. The heat may be added to the second surfactant using any suitable means as understood in the art. For example, the second surfactant may be heated using an autoclave, a hotplate, an open flame, an oven, a microwave, and the like. The heat may be added in order to melt and/or dissolve the second surfactant.

Embodiments of step S9050 may include combining the formed micelles and the second surfactant, thereby forming a mixture that includes the micelles formed from the first surfactant solution and the second surfactant solution.

Embodiments of step S9060 may include purging the surfactant mixture with a purging gas. The purging gas may include any suitable gas for purging as understood in the art, including, for example a perfluorocarbon, nitrogen, carbon dioxide, argon, helium, sulfur hexafluoride, or other suitable inert gas as understood in the art. The purging may be done under static conditions. The purging may be done under mixing or mechanical agitation. Embodiments of step S9070 may include mixing or agitating the purged mixture under a constant stream of the purge gas. For the purged mixture may be sonicated using a bath sonicator, a probe sonicator, or the like. The mixture may be mechanically agitated using one or more of a cell lysor, a disperser, a high shear mixer, homogenizer, a rotor stator homogenizer, and the like.

Embodiments of step S9080 may include separating the formed microbubbles below 10 μm in diameter. The formed microbubbles may be separated using an suitable technique including for example a separatory funnel in order to separate the microbubbles based on buoyancy, a gradient filter including for example a sucrose gradient, centrifugation, and the like.

Method 9000 may further include processing the formed and separated microbubbles in order to generate gas-filled microbubbles. Embodiments of step S9090 may include freeze-drying and capping the separated microbubbles under vacuum. The separated microbubbles may be freeze-dried using any suitable technique as understood in the art including, for example, using a spin-vacuum, a lyophilizer and the like. The freeze-dried microbubbles may be re-inflated with one or more gases or mixtures of gases. The one or more gases may include one or more of oxygen, carbon dioxide, nitric oxide, xenon, or one or more suitable blood gas mixtures as understood in the art, and/or one or more combinations thereof.

EXPERIMENTAL EXAMPLES

Figure 1:
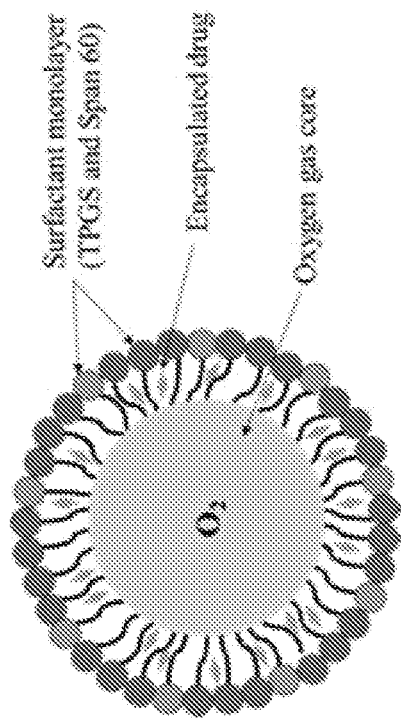
FIG. 1 depicts a schematic of drug loaded $SE61_{O2}$ microbubbles (MB) together with formulae of major components.
Figure 1:
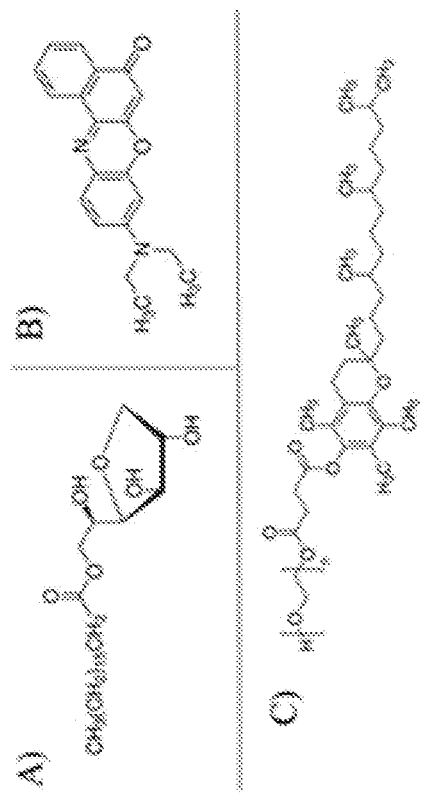

Example 1: Synthesis of Surfactant-Stabilized Oxygen Microbubbles that Accommodate Encapsulated Drug Introduction The contrast agent $SE61_{O2}$ is comprised of a sorbitan monostearate and water-soluble vitamin E (D-α-Tocopherol polyethylene glycol 1000 succinate, abbreviated as TPGS) shell around an oxygen core (FIG. 1). Sorbitan monostearate is a water insoluble, nonionic surfactant that is widely used in pharmaceutical applications. TPGS is an amphipathic and nonionic, water soluble molecule that has been shown to increase bioavailability and cellular uptake when incorporated into drug delivery platforms (Muthu, M. S. et. al. Biomaterials, 2015. 39: 234-248) TPGS also acts as a P-glycoprotein inhibitor to overcome multi-drug resistance (MDR) in tumors and is able to induce reactive oxygen species (ROS) to generate cancer cell apoptosis (Yang, C. et. al. Theranostics, 2018. 8(2): 464-485). TPGS micelles have been shown to solubilize hydrophobic drugs and have been used to deliver chemotherapeutic agents such as cisplatin, docetaxel and paclitaxel (Muthu, M. S. et. al. Biomaterials, 2015. 39: 234-248; Guo, Y. et. al. European journal of pharmaceutical sciences, 2013. 49(2): 175-186; Mi, Y. et. al. International journal of pharmaceutics, 2012. 438(1-2): 98-106; Yang, C. et. al. Theranostics, 2018. 8(2): 464).

SE61 is fabricated initially with a perfluorocarbon (PFC) gas core to achieve maximum MB yield, but this gas is removed during lyophilization, leaving a hollow microsphere into which other gases can be reintroduced (McDonald, P. C. et al. Frontiers in cell and developmental biology, 2016. 4: 27). The MB shell consists of hydrophobic fatty acid chains which could accommodate a hydrophobic drug (FIG. 1). There is therefore a need to design a method to maximize drug encapsulation in SE6102, employing a protocol that does not utilize toxic chemicals. Here it is shown that the redesigned SE61 manufacturing protocol which takes advantage of the formation of TPGS micelles to solubilize a hydrophobic drug. This methodology is informed by the knowledge that since the concentration of TPGS used to fabricate SE61 is greater than the critical micelle concentration (CMC) of TPGS (0.003% at 22° C. and 0.02% at 37° C.), micelles must be present in the mixture prior to sonication. Capitalizing on the fact that drug loaded TPGS micelles have been described, it is a logical choice for these drug loaded micelles to be investigated for use in the fabrication of SE61 (Yang, C. et. al. Theranostics, 2018. 8(2): 464-485).

As a model hydrophobic drug we chose Nile red (NR), which has a molecular weight of 318, similar to that of small molecular weight chemotherapeutics such as lonidamine (322), and cisplatin (300). Nile red (9-diethylamino-5H-benzo[α]phenoxazine-5-one) (FIG. 1) is fluorescent and is used as a hydrophobic probe due to this fluorescence being dependent on the polarity of its environment (Fowler, S. D. and P. Greenspan. The Journal of Histochemistry and Cytochemistry, 1985. 33(8): 833-836.). In aqueous solutions, NR fluorescence is quenched, with the intensity being 40-fold less than in nonpolar solvents (Fowler, S. D. and P. Greenspan. The Journal of Histochemistry and Cytochemistry, 1985. 33(8): 833-836; Greenspan, P. and S. D. Fowler, Journal of Lipid Research, 1985. 26: 781-789). In nonpolar solvents and in the presence of lipids, NR fluoresces red, but as the solvent becomes more polar, the fluorescence experiences a blue shift and fluoresces golden-yellow. Thus, when encapsulated in the shell of SE61, it is expected that NR will fluoresce red when intercalated into the hydrophobic region of the MB shell. This property makes NR an ideal model hydrophobic drug, as it can be easily quantified and visualized in both micelles and in the MB shell.

Materials and Method

Materials

Sorbitan monostearate (MONTANE® 60 PHA, Premium, Seppic, France). TPGS (EASTMAN CHEMICAL COMPANY™, Kingsport, TN). Octafluoropropane (PFC) (SPECIALTY GASES OF AMERICA™, Reno, NV), oxygen, (AIRGAS®, Radnor, PA). Both gases were passed through a 0.2 µm sterile filter prior to use (NALGENE®, Rochester, NY). COUNTBRIGHT® absolute counting beads (C36950, $0.54 \times 10^5$ beads/50 µL) used as a reference standard for flow cytometry (LIFE TECHNOLOGIES®, Grand Island, NY). All other chemicals were from MILLIPORE SIGMA® (Darmstadt, Germany) were used as received.

Methods

Standard SE61 Microbubble Fabrication

Surfactants sorbitan monostearate, and TPGS in the molar ratio of 4:1, and sodium chloride (1.5 g) were combined and melted in a tall 250 mL beaker prior to the addition of 50 mL of warm (37° C.) phosphate buffered saline (PBS). This mixture was stirred and heated until a homogenous solution was obtained and then was autoclaved for 35 minutes at 17-21 psi to allow for better dispersion of MONTANE® 60. After autoclaving, the solution was allowed to cool to room temperature while stirring rapidly on a magnetic stirrer. Once cooled, the beaker containing the mixture was placed in an ice bath and purged with PFC gas. The solution was then sonicated at 20 kHz for 3 minutes at 110 W using a 0.5" probe horn (MISONIX®, Inc., Farmingdale, NY), while being continuously purged with PFC gas. The mixture was then transferred to a 250 mL glass separatory funnel to allow the formed MBs to separate based on buoyancy. The MBs were washed three times with cold (4° C.) PBS, with a 90 minutes separation between the first two washes and a 60 minutes separation after the third wash, and discarding the lower PBS layer each time.

SE61 Microbubble Fabrication with TPGS Micelles

Sorbitan monostearate and sodium chloride were prepared as above. The TPGS micelles were formed by dissolution in 25 mL warm (37° C.) PBS followed by stirring for at least 20 minutes. The TPGS micelle solution was added to the Montane 60 solution after the autoclave step and the combined mixture was stirred until cooled to room temperature (24° C.).

Drug Loaded SE61 MB

For the standard SE61 fabrication method, drug was added to the sorbitan monostearate/TPGS solution immediately after the autoclave step. Nile red was added as a 1 mg/mL solution in methanol to help solubilize the hydrophobic drug, and to facilitate addition of a more consistent quantity. For the method using TPGS micelles, the drug was added as a powder to the TPGS solution once the TPGS had dissolved (after about 20 minutes of stirring). The drug-TPGS solution was then added to the sorbitan monostearate solution after the autoclave step while still hot.

Freeze Drying

Once the third separation was complete, the MB-rich layer was collected and diluted 1:1 (v/v) with a 10% (w/v) glucose-water solution, yielding a final glucose concentration of 5% (w/v)) to act as a lyoprotectant. Aliquots of 4 mL of the resulting solution were pipetted into 20 mL lyophilization vials (WEST PHARMACEUTICAL SERVICES, Lionville, PA) and subsequently frozen in a 1:1 water-propylene glycol recirculating bath (Haake D1 and G, Germany) set to −20° C. Once frozen, the vials were loosely sealed (to the first groove) with stoppers (DWK LIFE SCIENCES®, Inc., Millville, NJ) and then placed on a pre-chilled (−20° C.) shelf assembly that allowed for sealing under vacuum. The MBs were then lyophilized using a VIRTIS® Benchtop freeze dryer (Gardiner, NY) for 20 hours with a condenser temperature less than −70° C. and pressure below 100 µbar. After 20 hours, the vials were sealed under vacuum, removed from the freeze dryer, further sealed with Parafilm, and then stored at −20° C. until use.

Reconstitution

Prior to testing, freeze dried samples were prepared by introducing oxygen (passed through a 0.2 µm sterile filter) into the vial using a sterile needle through the stopper at about 50 mL/min for approximately 30 s and then reconstituting the MBs in 4 mL of 0.5×PBS, to achieve a final salt concentration of 1×PBS.

Acoustic Characterization

Acoustic Setup

In vitro acoustic testing was performed in a previously described custom-built setup designed to closely mimic in vivo conditions, with a tank filled with DI water at 37° C. Samples were pipetted into an acrylic sample holder with an acoustically transparent window that was filled with 50 mL 1×PBS (37° C.). A 5 MHz transducer (Olympus, Waltham, MA) with a focal length of 49.3 mm, a 12.7 mm diameter, a center frequency of 5.15 MHz, and a −6 dB bandwidth of 82.46% was used and a PANAMETRICS® pulser/receiver (model 5072PR) was used to generate pressure amplitudes with a PRF of 100 Hz at energy level 1, resulting in a peak positive pressure (PPP) of 0.69 MPa and a PNP of 0.25 MPa. The signals were amplified 40 dB and read using a LECROY® 9350A digital oscilloscope (Chestnut Ridge, NY). The data were processed using LABVIEW® (NATIONAL INSTRUMENTS®, Austin, TX).

Dose Response

For dose response curves (at 37° C.), which represent the enhancement of the signal returned to the transducer as a function of MB dose, $SE61_{O2}$ was pipetted into the sample holder containing 50 mL of PBS, in increasing doses. Between each dose, the PBS in the sample holder was replaced with new PBS.

Time Response

For time response testing, which was performed to evaluate the stability of the MBs under continuous insonation at 37° C., a single dose along the rise of the dose response curve (in this case, 180 µL/L) was pipetted into the sample holder and insonated for 10 min. Measurements were taken each minute, starting at t=0, for a total of 11 readings. The data were normalized to the initial reading at t=0 to allow for comparison of stability between batches.

Flow Phantom

Echogenicity and MB destruction-under near physiological conditions were also assessed for the MBs, using a flow phantom and clinical scanner. Empty and drug loaded MBs were evaluated at room temperature using an ACUSON S3000® ultrasound System HELX™ Evolution scanner, (SIEMENS® Medical Solutions, Mountain View, CA), equipped with a 9 L probe (SIEMENS®), operating in nonlinear contrast imaging mode, and a tissue mimicking flow phantom (ATS Laboratories, Bridgeport, CT, model 524) with a 6 mm diameter vessel embedded at a depth of 2 cm. A concentration of $1.0 \times 10^7$ MBs in 800 mL PBS was loaded onto the phantom, circulated using a peristaltic pump at 23 rpm, 350 mL/min. Samples were standardized to MB concentration per milliliter so that the same number of MBs were passing through the phantom in each test. Images of flash replenishment were captured through a DICOM clip. Contrast mode images were taken every 30 seconds post injection, over a 20 min period.

Physical Characterization

Microbubble Size and Polydispersity

Size and polydispersity were determined using dynamic light scattering (DLS), measured using a ZETASIZER® Nano ZS (MALVERN INSTRUMENTS™, Worcestershire, UK). Samples were prepared by dispersing 50 µL of reconstituted MBs in 950 µL of 1×PBS and were measured at 25° C. MB size was reported as the z average.

Light Microscopy

An Olympus IX71 fluorescence microscope (Olympus Corporation, Tokyo, Japan) was used to obtain images of the MBs and qualitatively assess Nile loading via fluorescence. Images were obtained using Olympus cell Sens Standard software (Olympus Corporation, Tokyo, Japan).

Microbubble Counting

Counting was completed using a LSRII flow cytometer (BD Biosciences, San Jose, CA). Samples were prepared for analysis by adding 10 µL of reconstituted MBs to 500 µL of water and 10 µL of UV COUNTBRIGHT® counting beads (containing 10,800 beads as a counting standard). FLOWJO® software (Tree Star, Inc., Ashland, OR) was used for data analysis. First, the MBs and counting beads were separated using forward scattering (FSC-A) and fluorescence (FITC-A gate). Then, once this gate was applied, the MBs were plotted using FSC-A versus side scattering (SSC-A) and the MB counts were determined. The data were then separated into four regions of interest based on density to observe changes in the MB populations.

Shell Composition

Proton Nuclear Magnetic Resonance

Samples were prepared for $^1$H NMR (nuclear magnetic resonance) by dissolving 10-15 mg of freeze dried MBs (prepared using the protocols for the standard and micelle methods, with the exception that lyoprotectant was not added prior to freezing, so that the analyzed mixture contained only SPAN® 60, TPGS, and PBS salts), in chloroform-din NMR tubes. The initial analysis of the surfactants (sorbitan monostearate and TPGS) was performed on a 300 MHz VARIAN Utility Inova NMR system (AGILENT TECHNOLOGIES®, Santa Clara, CA) and analysis of the MBs was done using a 500 MHz VARIAN® Utility INOVA™ NMR system (AGILENT TECHNOLOGIES®, Santa Clara, CA). Spectra from the MB were obtained using a high resolution NMR systems using VnmrJ 4.2 (AGILENT TECHNOLOGIES®, Santa Clara, CA) and were analyzed using Mnova 11.0 (MESTRELAB RESEARCH®, Santiago de Compostela, Spain).

Drug Loading Quantification

For NR quantification, MBs were dissolved in 4 mL of methanol. A 1 mL aliquot was transferred to a microcentrifuge tube and centrifuged at 1,000 rcf for 2 min to pellet undissolved Montane 60, which is insoluble in methanol. The resulting supernatant was diluted 1:7 with methanol in order to bring the sample within the range of the standard curve, and 100 μL of each sample was plated in a COSTAR® 96 well black opaque plate (CORNING® Inc., Corning, NY) in triplicate. A standard curve of NR in methanol was also constructed for concentrations ranging from 0.01 μM to 50 μM using a serial dilution. Fluorescence intensity was measured in triplicate using a Synergy H1 microplate reader (BIOTEK INSTRUMENTS™, Winooski, VT) ($\lambda_{excitation}$: 550 nm, $\lambda_{emission}$: 650 nm). Encapsulation efficiency of NR in the MBs was calculated using the equation.

$$\% \text{ Encapsulation Efficiency} = \frac{\text{Mass of } NR \text{ in } MBs \text{ (mg)}}{\text{Initial Mass } NR \text{ Added (mg)}} \times 100 \quad (1)$$

Statistical Analysis

All data were presented as the standard deviation about the mean, calculated using MICROSOFT® Excel (MICROSOFT OFFICE 365® Plus) (Microsoft Corporation, Redmond, WA). Statistical significance between maximum acoustic enhancement measurements, as well as size and PDI measurements for unloaded MBs were determined using an independent samples t-test, while differences between MB concentrations were determined using a two-way ANOVA. Statistical significance between unloaded and NR-loaded MBs in terms of maximum acoustic enhancement measurements and size measurements were determined using a two-way ANOVA. Significance for NR loading results between MBs made with the standard method and those made with the TPGS micelle method, as well as significance of PDI measurements between NR-loaded MBs made with both methods, were determined using an independent samples t-test. All statistical analyses were run on N=3, with a significance level of α=0.05, using SPSS 25 (IBM, Armonk, NY).

Results and Discussion

Comparing Standard and Micelle Method for Unloaded $SE61_{O2}$

Initial runs without drug indicated that both the standard methods and the new TPGS-micelles method produced MBs. However, it was observed that during the wash steps, of the two, MBs made with the TPGS-micelle method had a much clearer line of separation between the middle, MB-rich layer and the lower, PBS wash layer, suggesting that MBs made with the TPGS-micelle method may be more buoyant or more numerous.

Acoustical Characteristics

Dose Response Curves

Figure 2A:
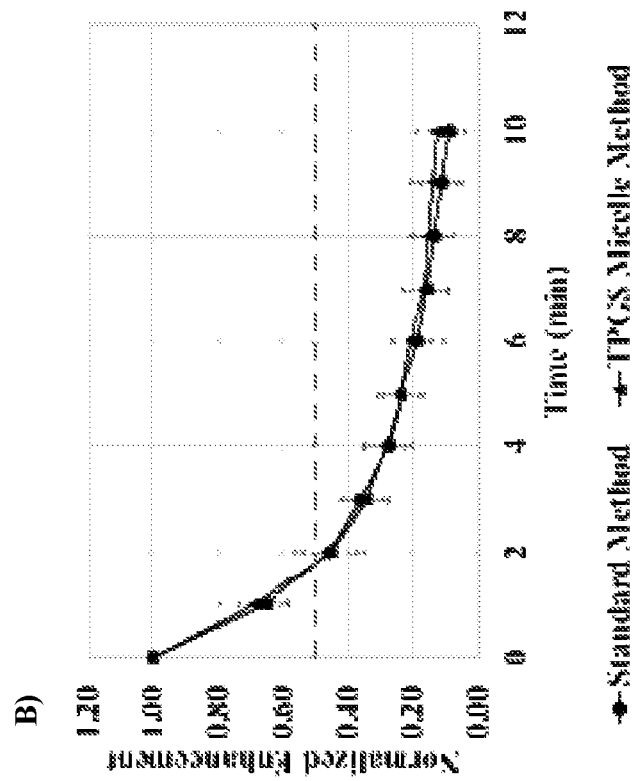
FIGS. 2A and 2B depict acoustic properties of reconstituted MB.

FIG. 2A shows the dose response curves from these two preparations after reconstitution in PBS. The average maximum enhancement (FIG. 2A) were statistically the same (p=0.892) (standard method 19.66±0.66 dB, micelle-method (19.62±0.65 dB). Notably, the shape of the dose response curves differs, with the maximum enhancement occurring at different doses for the two methods (980 μL/L vs. 280 μL/L), and considerable reduction of signal at high doses (shadowing) is seen in the dose response curve for the TPGS micelle method. Both of these results suggest that the micelle method yields a higher concentration of MBs. Consistent with previous results reported by the our group, it was also noted that the maximum enhancement for MBs fabricated by both methods (data not shown) was lower after freeze drying and reconstitution, attributed to a loss of a population of MBs during these steps. Pre-freeze drying enhancements were for the standard method, an average maximum of 22.64±0.72 dB, at a dose of 190 μL/L while for micelle method the average maximum enhancement was 21.53±1.60 dB at a dose of 90 μL/L. There was again no significant difference between the maximum enhancements of the two methods (p=0.334).

Time Response Curves

Figure 2B:
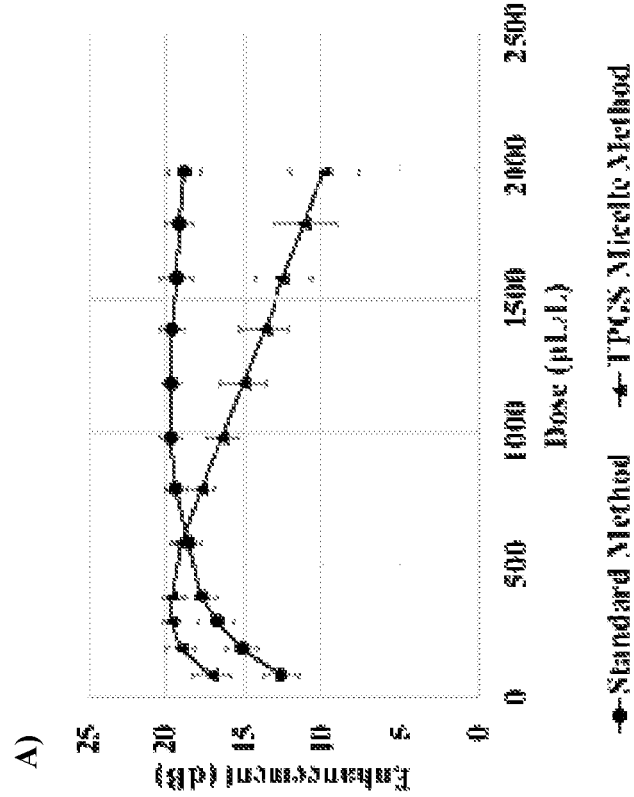

Time response curves on the other hand, overlap for the two methods (FIG. 2B), with a half-life (time for normalized enhancement to drop to 0.5) between 1.5 and 2 min for both MB fabrication methods, indicating that changing the methodology does not impact stability of the MBs.

Flow Phantom Analysis

Figure 3:
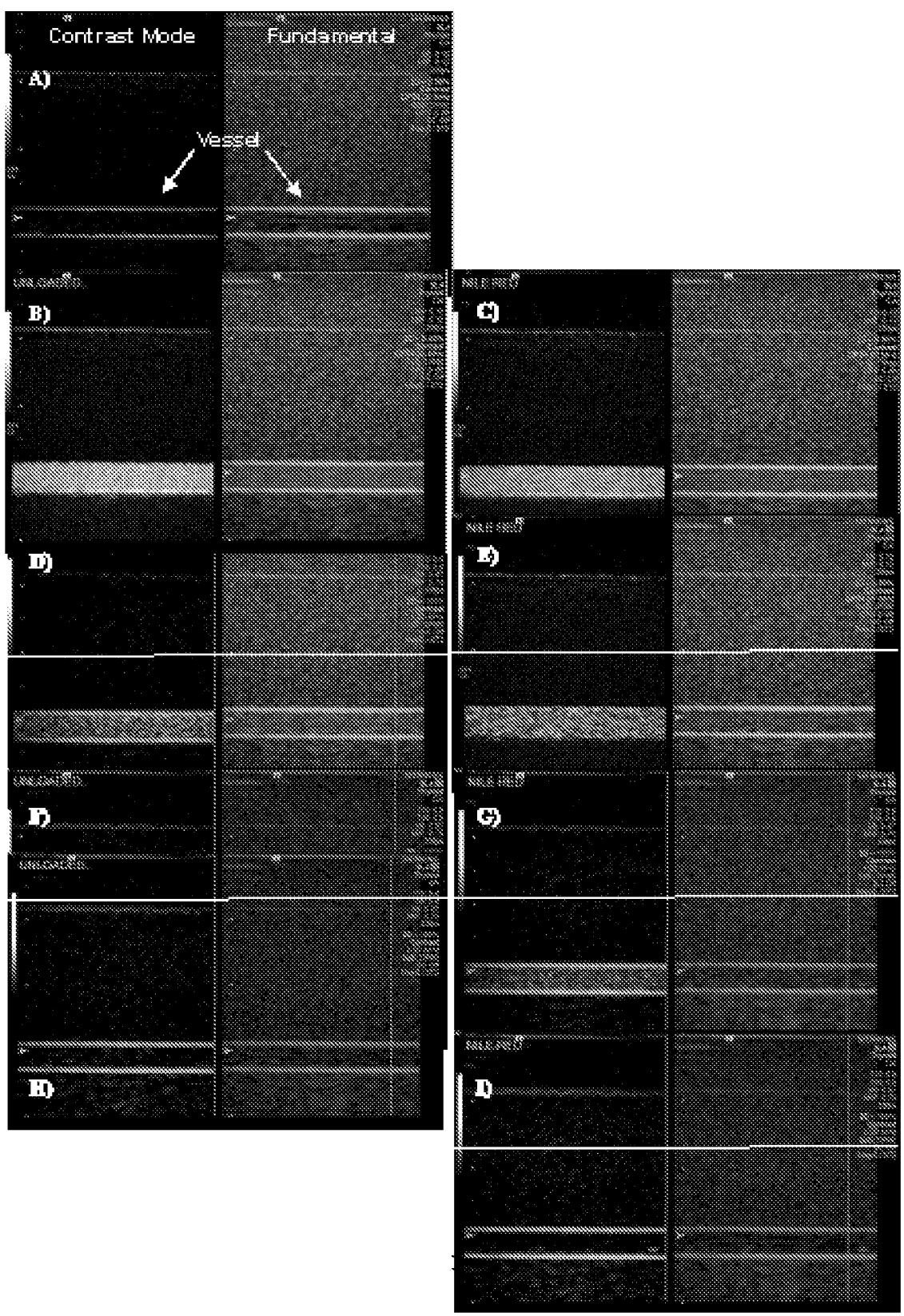
FIG. 3 depicts images from a tissue-mimicking flow phantom using unloaded MBs (left hand column) and MBs loaded with Nile red (right hand column). Each image was taken at a focal length of 4 cm, displayed in both non-linear contrast mode (left hand image) and fundamental B-mode (right hand image), starting with pre-injection, empty vessels taken as the baseline images.

To obtain a concept of the potential for imaging in a clinical setting, both unloaded and NR loaded MBs were visualized in a tissue-mimicking flow phantom with an US scanner used for clinical imaging. Using a linear US transducer, images were obtained in both B-mode (FIG. 3 Right image) and contrast-mode (Left image), at a focal length of 4 cm. A Baseline pre-injection image is shown at the top of each panel. The images clearly show that both forms of the MBs function well as contrast agents, and that both are completely destroyed in the US beam at higher MI.

Physical Characteristics

Size

Differences in measured size after freeze drying and reconstitution were not significant between the two methods (Table 1). $SE61_{O2}$ MBs made with the standard method had an average diameter of 1.63±0.53 μm, while MBs made with the TPGS micelle method had an average of 1.57±0.39 μm (p=0.8). Interestingly, there was a shift in the size after freeze drying in both cases. The average MB size increased after freeze drying, (from 1.13±0.27 μm for the standard method and 0.94±0.29 μm for the micelle method). This could indicate that the loss of MBs during freeze drying is size-sensitive, but probably also reflects the fact that prior to freeze drying the bubbles contain the hydrophobic gas PFC, and upon reconstitution they contain oxygen.

Polydispersity Index

Measured PDIs of MBs prior to freeze drying were significantly different, 0.57±0.22, vs. 0.16±0.10, (p<0.001). This indicates that the TPGS micelle method produced a more monodisperse population. The PDIs drew closer together after freeze drying, with PDI for the standard method, being 0.19±0.12, while the PDI for the TPGS micelle method was 0.29±0.13. There was no significant difference between the PDI values after reconstitution (p=0.108). The shifts in PDI suggest that bubble size may influence freeze drying stability as suggested above.

Light Microscopy

Figure 5:
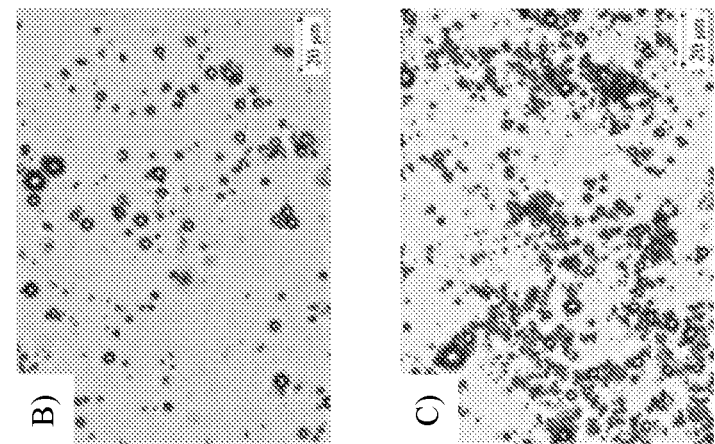
FIG. 5, Panel A depicts a dose response curve of $SE61_{O2}$ by the standard and micelle method, plotted by bubble number.
Figure 5:
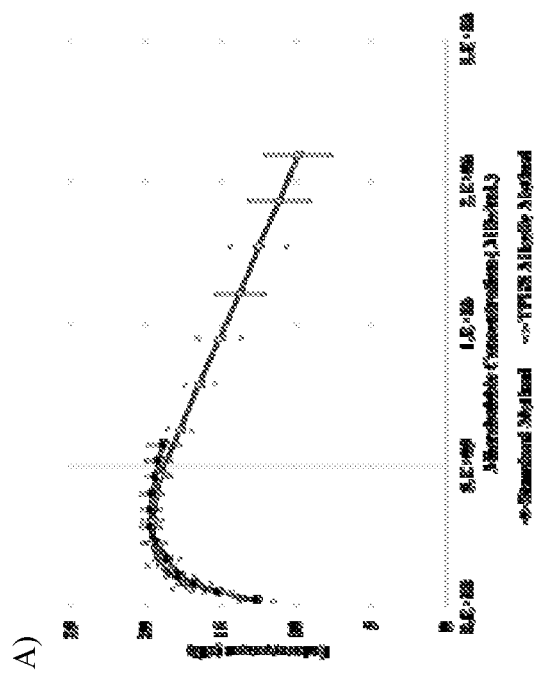

Light microscopy images of the same volume of reconstituted $SE61_{O2}$ MBs made by both methods can be seen in FIG. 5B. The higher micelle-MB concentration and similar overall size are clearly seen, less so the polydispersity.

These data suggest that the MBs made by both methods initially produce different populations of MB but with similar shells. However further analyses (MB count and $^1H$ NMR) were performed to investigate this further.

Population Dynamics

Starting with the same quantities of materials, MB concentrations were measured for each method by conducting a count using a flow cytometer. To account for the possibility that the TPGS-micelle method produces MBs that are more robust during freeze drying, samples taken before freeze drying were included in the analysis, remembering that the pre-freeze dried samples contain PFC not oxygen. The MB counts for both methods, both pre- and post-freeze drying, are summarized in Table 1.

TABLE 1

Effect of SE61 fabrication method on size, PDI, and microbubble count data prior to and after freeze drying (FD)

|  |  | Size (μm) | PDI | Total Microbubbles/mL | Microbubbles/mL Q1 | Microbubbles/mL Q4 |
|---|---|---|---|---|---|---|
| Standard | Pre-FD | 1.13 ± 0.27 | 0.19 ± 0.12 | (7.40 ± 0.83) × $10^8$ | (4.39 ± 0.50) × $10^8$ | (2.45 ± 0.28) × $10^8$ |
|  | Post-FD | 1.63 ± 0.53 | 0.57 ± 0.22 | (2.91 ± 0.48) × $10^8$ | (1.26 ± 0.22) × $10^8$ | (1.43 ± 0.24) × $10^8$ |
|  | Change | — | — | −60.68% | −71.30% | −41.63% |
| TPGS Micelle | Pre-FD | 0.94 ± 0.29 | 0.29 ± 0.13 | (16.16 ± 0.45) × $10^8$ | (9.16 ± 0.29) × $10^8$ | (6.30 ± 0.24) × $10^8$ |
|  | Post-FD | 1.57 ± 0.39 | 0.16 ± 0.10 | (8.05 ± 0.99) × $10^8$ | (3.60 ± 0.47) × $10^8$ | (4.09 ± 0.50) × $10^8$ |
|  | Change | — | — | −50.18% | −60.70% | −35.08% |

Prior to freeze drying, $SE61_{PFC}$ MBs made with the standard method had a concentration of $(7.40\pm0.83)\times10^8$ MBs/mL, while those made with the TPGS micelle method were almost twice as concentrated and had a concentration of $(16.16\pm0.45)\times10^8$ MBs/mL. After freeze drying, $SE61_{O2}$ MBs made with the standard method had a concentration of $(2.91\pm0.48)\times10^8$ MBs/mL, while those made with the TPGS micelle method had a concentration of $(8.05\pm0.99)\times10^8$ MBs/mL. A two-way ANOVA was run to determine if fabrication method and lyophilization significantly affected MB concentration. It was found that there was a statistically significant interaction of the effects of fabrication method and lyophilization on the MB concentration ($F(1,20) = 37.526$, $p<0.001$). The concentration of MBs made with the TPGS micelle method was significantly higher than that of the MBs made with the standard method ($p<0.001$). This was true both prior to ($7.40\pm0.83\times10^8$ vs. $16.16\pm0.45\times10^8$) and post freeze drying, ($2.91\pm0.48\times10^8$ vs. $8.05\pm0.99\times10^8$) indicating that the TPGS micelle method increases the overall yield of MBs from the start. Changing how the two surfactants are initially mixed prior to sonication impacts MB formation, increasing yield. Additionally, as expected, the concentration of MBs was greater in both cases prior to freeze drying than after freeze drying and refilling with oxygen ($p<0.001$). There was also a greater loss of MBs after freeze drying for the standard method (−60.68%) than with the TPGS micelle method (−50.18%), which could account for the differences in PDI between the two methods, and indicate that bubble destruction during processing may be size-dependent.

Figure 4:
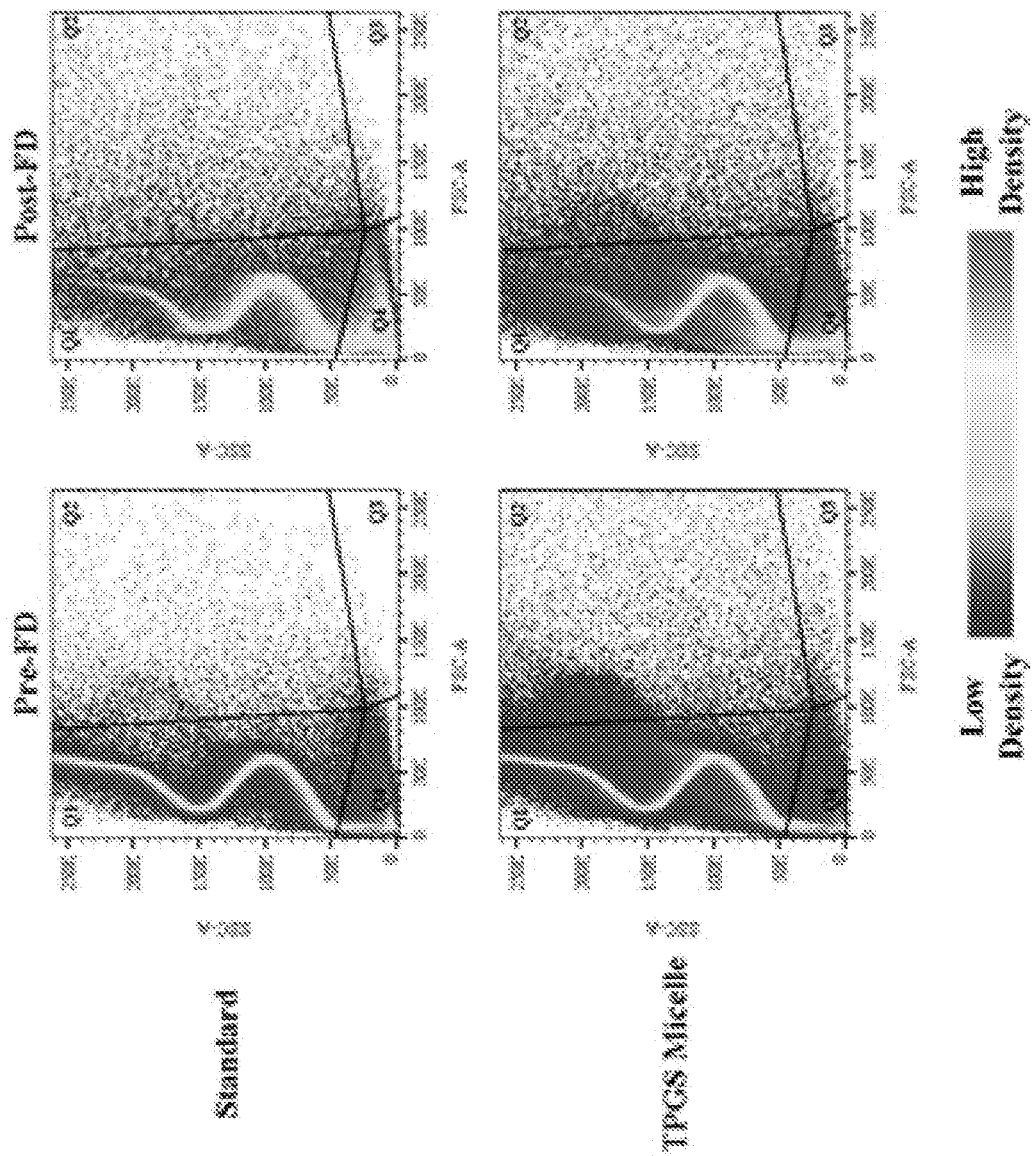
FIG. 4 depicts representative flow cytometry data showing count density. The plots show forward scattering (FSC-A) versus side scattering (SSC-A) for SE61 made with the standard and TPGS-micelle methods prior to and after freeze drying (FD).

Representative plots, showing count density can be seen in FIG. 4 (and quadrant data in Table 1). When analyzing the density by quadrant, previous results suggest that quadrant 1 (Q1) contains a more echogenic population of MBs, while quadrant 4 (Q4) is believed to contain a population of small, less echogenic particles. The TPGS micelle method results in a smaller reduction in the number of MBs in Q1 after freeze drying than the standard method, (61% compared to 71% change), as well as a smaller reduction in the population (Q4) of less echogenic particle (35% compared with 42%). This result, together with the influence of the fabrication method on the bubble concentration and PDI after freeze drying, suggests that the TPGS micelle method not only contributes to an increased number of MBs collected, but also has some influence on the stability of the MBs during freeze drying, either as a direct result of increased concentration leading to steric stabilization, a change in the nature of the MB shells, production of different sized populations in which the standard method produces more MBs that are more susceptible to destruction during freeze drying, or, conversely, the TPGS micelle method produces a population that is more stable to freeze drying.

Replotted Acoustic Data

Based on these findings the dose response curves were replotted by bubble number, resulting in the overlap of the two curves, (FIG. 5A). The light micrographs taken of equal volume sample of microbubbles, taken after reconstitution, visually confirm that the micelle method produces a greater number of MBs, (FIGS. 5B and 5C).

Shell Composition by $^1$H NMR

Figures 6A, 6B, 6C:
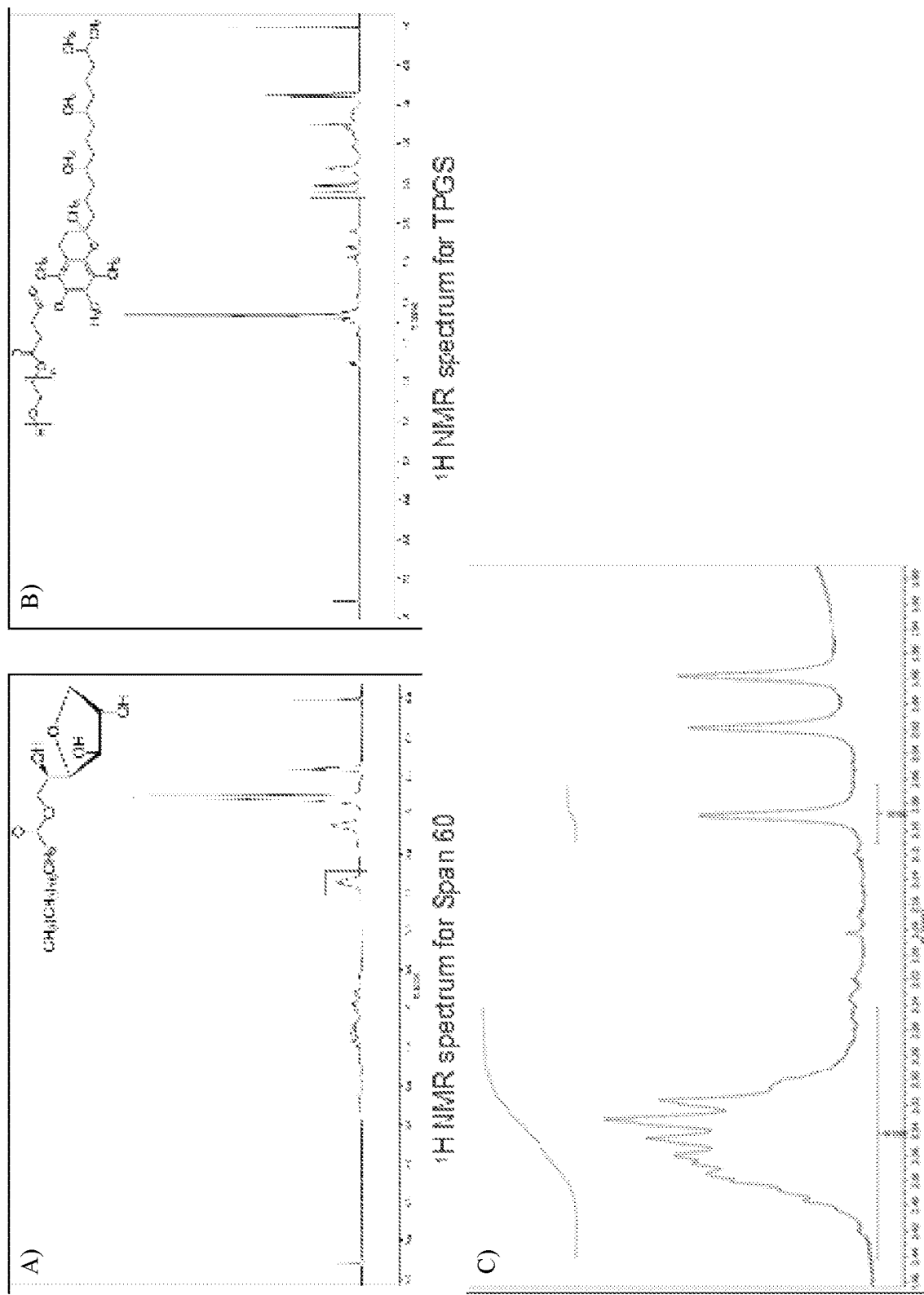
FIG. 6 depicts $^1H$ NMR spectra for the two surfactants.

The $^1$H NMR spectra obtained for the two individual surfactants identified the peak of interest for MONTANE® 60 at δ=2.35 ppm, which corresponds to the two hydrogens attached to the carbon atom next to the ester group (FIG. 6A), and δ=2.10 ppm for TPGS, corresponding to the three hydrogens on the methyl group attached to the benzene ring (FIG. 6B). To confirm that integrating the two chosen peaks resulted in an accurate determination of molar ratio between MONTANE® 60 and TPGS, a sample made up of a known molar ratio of the two (3.83:1) was analyzed via NMR. After integration of the peaks of interest in the resulting spectrum, the calculated molar ratio was 3.8:1. This suggests that using these peaks to determine the ratio of MONTANE® 60 to TPGS yields an accurate result.

The peaks of interest in SE61 samples were integrated as shown in FIG. 6C, and the calculated surfactant ratios can be seen in Table 2. The three SE61 samples analyzed for the standard method had molar ratios of sorbitan monostearate to TPGS of 12.97:1, 15.32:1, and 15.15:1. The samples analyzed for the TPGS micelle method had sorbitan monostearate to TPGS molar ratios of 18.10:1, 16.57:1, and 16.05:1.

The calculated molar ratios of the surfactants in MBs made by both methods are not significantly different (p=0.079), with the standard method at 93.5±0.6% sorbitan monostearate, and the micelle method giving 94.4±0.6% sorbitan monostearate) suggesting that the composition of the MB remains virtually the same between the two methods.

Standard Vs. Micelle Method for $SE61_{O2}$ with Loaded Model Drug

Operational Observations

Having identified that the micelle method produces roughly double the MB yield, it was important to ascertain what effect the change in method had on drug encapsulation.

Based on previous work in our group, 3.9 mg of NR (250 µM drug starting concentration) was added to the surfactant mixture prior to sonication for both methods.

In the standard method, Nile red was added in methanol (deep red solution). For the micelle method, NR was added to the TPGS micelle solution as a dry powder, and the solution turned from clear to pink indicating that Nile red is in a hydrophobic environment, and therefore has been solubilized by the TPGS micelles. The color deepened upon addition of MONTANE® 60 solution. As before, during bubble separation the micelle method gave a much clearer line of separation, and both methods gave a pink cake upon freeze drying, indicating that the drug is still associated with a hydrophobic environment.

Acoustical Characteristics

Dose Response Curves

The dose response curves obtained from the reconstituted NR-SE61$_{O2}$ was identical to the unloaded agents for both methods (graphs not shown). The standard method produced an average maximum enhancement of 19.37±0.67 dB at a dose of 1380 µL/L, while the micelle method had an average maximum enhancement of 19.81±1.09 dB, at a dose of 280 µL/L. A two-way ANOVA found that there was no statistically significant interaction of the effects of fabrication method and drug loading on the enhancement of the MBs ($F(1,32)=0.809$, $p=0.375$). There was no significant difference between the enhancement of MBs made with the two methods ($p=0.465$) and there was no significant difference between the enhancement of unloaded and drug loaded MBs ($p=0.857$). This difference in doses can be attributed once again to the higher concentration of MBs produced in the TPGS micelle method, as shown above with the MB counts.

Time Response Curves

Figure 7:
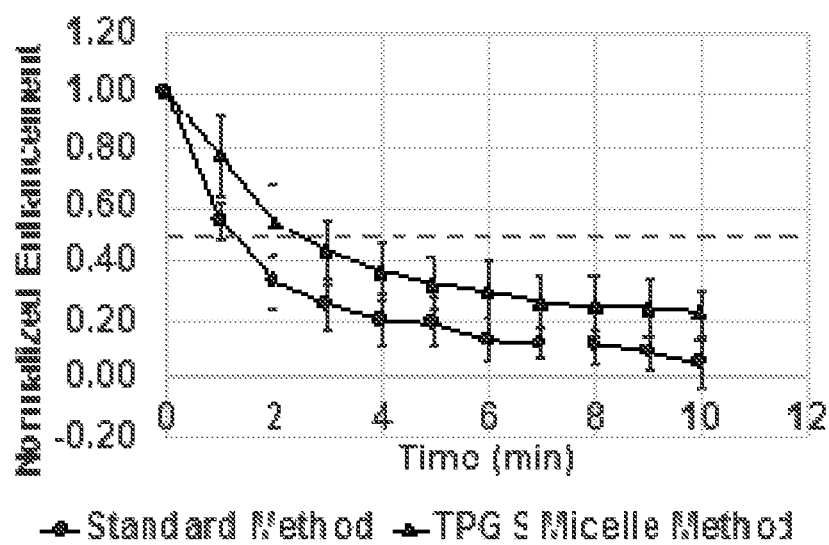
FIG. 7 depicts a comparison of the stability of empty and NR-loaded MB in the ultrasound beam.

Time response curves (FIG. 7), however, showed a half-life between 1.5 and 2 min for both MB fabrication methods, indicating that changing the methodology does not impact stability of the drug loaded MBs.

Drug Encapsulation

Loading Efficiency

As can be seen by Table 2, drug loading efficiency was significantly higher for the micelle method, ($p<0.01$) even taking into account the greater MB yield.

TABLE 2

NR encapsulation efficiency for SE61 MBs made with the standard and TPGS micelle methods (n = 3).

| Method | NR Added (mg) | NR Encapsulated (µg) | Encapsulation Efficiency |
|---|---|---|---|
| Standard | 3.9 | 154.08 ± 122.52 | 3.95% |
| TPGS Micelle | 3.9 | 409.06 ± 65.90 | 10.49% |

Upon reconstitution, the standard method resulted in a Nile red concentration of 5.39±4.17 µg/mL, while the TPGS micelle method had a concentration of 13.58±3.52 µg/mL.

The encapsulation efficiency of Nile red loading is more than doubled with the TPGS micelle method (10.49%) compared to the standard method (3.95%). However, when the Nile red concentration is normalized by the average MB concentration, there is no significant difference in Nile red loading between the standard method (($1.86\pm1.43)\times10^8$ µg/MB) and the TPGS micelle method (($1.69\pm0.44)\times10^8$ µg/MB) ($p=0.739$), suggesting that the increase in loading per batch is a result of increased MB yield, and also that pre-loading the micelles with drug does not compromise the loading.

Conclusions

In an effort to improve drug encapsulation efficiency in surfactant-stabilized MBs, a new method of fabrication was investigated by first creating drug-loaded micelles with the TPGS component of a dual component MB shell. Although the resulting MBs had similar shell composition, and physical and acoustic properties, the yield was over 50% higher, resulting in a similar dramatic increase in encapsulation efficiency upon inclusion of drug. The reason for the dramatically increased MB yield when TPGS is allowed to form micelles prior to mixing with the sorbitan monostearate is not clear. Without wishing to be bound to theory, it is possible that the stability during freeze drying is very sensitive to MB size and that the TPGS micelle method produces a larger proportion of the more stable size, based on the MB population dynamics observed with the flow cytometry results. Alternatively, the pre-formed micelles and Montane 60 present themselves in the initial sonication mixture in a manner that is more conducive to reassembly around the hydrophobic PFC gas bubbles which are forced from the solution by the ultrasound. It is clear that the higher number of bubbles facilitates the separation process. The exact mechanism is the subject of further investigation While an increased drug loading per MB was not encountered, which may have had clinical advantages, increased encapsulation efficiency is important and becomes highly significant when considering high value bioactive species to be encapsulated. The results also highlight the importance of considering all aspects of a manufacturing process.

EQUIVALENTS

Although preferred embodiments of the invention have been described using specific terms, such description is for illustrative purposes only, and it is to be understood that changes and variations may be made without departing from the spirit or scope of the following claims.

INCORPORATION BY REFERENCE

The entire contents of all patents, published patent applications, and other references cited herein are hereby expressly incorporated herein in their entireties by reference

The invention claimed is:

1. A method for preparing acoustically-sensitive microbubbles, the method comprising:
   (i) preparing a first surfactant solution comprising a first micelle-forming surfactant at a concentration above the critical micelle concentration (CMC);
   (ii) adding one or more pharmaceutical compounds in a solvent to the first surfactant solution, thereby loading the micelles with the one or more pharmaceutical compounds;
   (iii) preparing a second surfactant solution comprising a second surfactant, wherein the second surfactant comprises one or more matrix-forming surfactants;
   (iv) adding heat to the second surfactant solution to melt the one or more matrix-forming surfactants and allowing the mixture to cool under rapid stirring;
   (v) combining the second surfactant solution with the loaded micelles;
   (vi) purging the surfactant mixture with a purging gas;
   (vii) agitating the purged mixture under a constant stream of the purging gas; and
   (viii) separating the formed microbubbles by size.

2. The method of claim 1, further comprising:
(ix) freeze-drying and capping the separated microbubbles under a vacuum.

3. The method of claim 2, further comprising:
(x) reinflating the freeze-dried microbubbles with a filling gas.

4. The method of claim 3, wherein the filling gas comprises oxygen.

5. The method of claim 1, wherein the first surfactant comprises TPGS, hexadelyltrimethylammonium bromide (CTAB), didodecyldimethylammonium bromide (DDAB) or mixtures thereof.

6. The method of claim 1, wherein the second surfactant comprises sorbitan monostearate, sorbitan fatty acid esters, sorbitan monopalmitate, (+) A tolopherol acid succinate (vitamin E) or mixtures thereof.

7. The method of claim 1, wherein the second surfactant is solid at room temperature.

8. The method of claim 1, wherein the second surfactant is immiscible in water.

9. The method of claim 1, wherein the drug-loaded microbubble solution comprises a drug-loading efficiency of about 10%.

10. The method of claim 1, wherein the CMC comprises 0.02 wt % at 37° C.

11. The method of claim 1, wherein the one or more pharmaceutical compounds comprise one or more chemotherapeutic agents.

12. The method of claim 11, wherein the one or more chemotherapeutic agents comprise lonidamine.

13. The method of claim 1, wherein the pharmaceutical compound comprises one or more tracing agents.

14. The method of claim 13, wherein the one or tracking agents comprise one or more lipophilic dyes.

15. The method of claim 14, wherein the one or more lipophilic dyes are selected from: Nile Red and DiI.

16. The method of claim 1, wherein the microbubbles are acoustically-sensitive.

17. The method of claim 1, wherein in step (viii) the size of the separated microbubbles is below 10 μm in diameter.

* * * * *